United States Patent [19]
Chambers et al.

[11] Patent Number: 5,919,783
[45] Date of Patent: Jul. 6, 1999

[54] INDOLINE AND AZAINDOLINE DERIVATIVES AS 5-HT$_{1D}$ ALPHA RECEPTOR AGONISTS

[75] Inventors: Mark Stuart Chambers, Puckeridge, United Kingdom; Victor Giulio Matassa, Rome, Italy; Leslie Joseph Street, Harlow, United Kingdom

[73] Assignee: Merck Sharp & Dohme Ltd., Hoddesdon, United Kingdom

[21] Appl. No.: 08/776,626

[22] PCT Filed: Jul. 24, 1995

[86] PCT No.: PCT/GB95/01756

§ 371 Date: Jan. 21, 1997

§ 102(e) Date: Jan. 21, 1997

[87] PCT Pub. No.: WO96/04269

PCT Pub. Date: Feb. 15, 1996

[30] Foreign Application Priority Data

Aug. 2, 1994 [GB] United Kingdom ............ 9415575

[51] Int. Cl.$^6$ .............. A61K 31/495; C07D 403/14; C07D 471/04
[52] U.S. Cl. ............ 514/253; 544/364; 544/366; 544/367; 544/369; 544/370; 544/373
[58] Field of Search ............ 544/366, 367, 544/369, 370, 371, 373, 364, 362; 514/253

[56] References Cited

U.S. PATENT DOCUMENTS

| | | | |
|---|---|---|---|
| 5,618,816 | 4/1997 | Crenshaw et al. | 514/253 |
| 5,807,857 | 9/1998 | Castro Pineiro et al. | 514/253 |

FOREIGN PATENT DOCUMENTS

| | | |
|---|---|---|
| 0 548 813 | 6/1993 | European Pat. Off. |
| WO 93/20073 | 10/1993 | WIPO |
| WO 94/02477 | 2/1994 | WIPO |

OTHER PUBLICATIONS

Forth, W. et al. Pharmakologie And Toxikologie (1987) pp. 16–17 in 'Allgemeine Pharmakologie', BI Publisher.

Hoyer, D. et al. Tips Reviews, "Partial agonists, full agonists, antagonists dilemmas of definition" vol. 14, pp. 270–274, Jul. 1993.

*Primary Examiner*—Emily Bernhardt
*Attorney, Agent, or Firm*—Philippe L. Durette; Melvin Winokur

[57] ABSTRACT

Compounds of formula (I), or a salt or prodrug thereof, wherein Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole, and tetrazole; E represents a chemical bond or a straight or branched alkylene chain containing from 1–4 carbon atoms; Q represents a straight or branched alkylene chain containing from 1–6 carbon atoms; T represents nitrogen or CH; R$^1$ represents aryl(C$_{1-6}$)alkyl or heteroaryl(C$_{1-6}$)alkyl, either of which groups may be optionally substituted; and R$^2$ represents hydrogen or C$_{1-6}$ alkyl are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

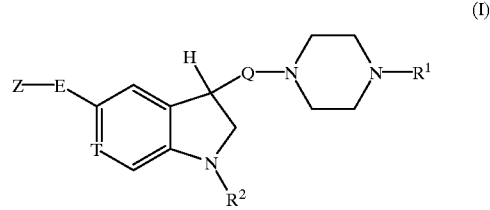

(I)

6 Claims, No Drawings

INDOLINE AND AZAINDOLINE DERIVATIVES AS 5-HT$_{1D}$ ALPHA RECEPTOR AGONISTS

The present invention relates to a class of substituted indoline and azaindoline derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0497512 and 0494774, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the indoline and azaindoline derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an optionally substituted arylalkyl or heteroaryl-alkyl substituent; nor of replacing the indole moiety with an indoline or azaindoline moiety; nor indeed is there any suggestion therein that the range of substituents specified at the 5-position of the indole moiety might be successfully replaced by an optionally substituted five-membered heteroaromatic ring.

Moreover, nowhere in the prior art available to date is there any disclosure of a subtype-selective 5-HT$_{1D}$ receptor agonist having a 5-HT$_{1D\alpha}$ receptor binding affinity (IC$_{50}$) of 50 nM or less and at least a 10-fold selective affinity for the 5-HT$_{1D\alpha}$ receptor subtype relative to the 5-HT$_{1D\beta}$ subtype.

The present invention provides a compound of formula I, or a salt or prodrug thereof:

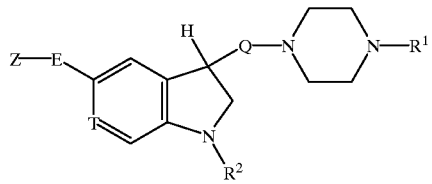

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms;

T represents nitrogen or CH;

R$^1$ represents aryl(C$_{1-6}$)alkyl or heteroaryl(C$_{1-6}$)alkyl, either of which groups may be optionally substituted; and R$^2$ represents hydrogen or C$_{1-6}$ alkyl.

The present invention also provides compounds of formula I above wherein T represents CH; and Z, E, Q, R$^1$ and R$^2$ are as defined above.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl.

The aryl(C$_{1-6}$)alkyl or heteroaryl(C$_{1-6}$)alkyl group R$^1$ may be optionally substituted, preferably on the aryl or heteroaryl moiety thereof, by one or more substituents. Examples of optional substituents on the group $R^1$ include halogen, cyano, trifluoromethyl, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

The compounds according to the invention have at least one asymmetric centre, and they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In particular, the carbon atom at the 3-position of the indoline or azaindoline nucleus in formula I above is an asymmetric carbon atom, thereby giving rise to the possibility of (R) and (S) enantiomers. It is to be understood that the present invention relates to the individual (R) and (S) enantiomers of the compounds of formula I as well as to all possible mixtures thereof, including racemic mixtures thereof.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E and Q, which may be the same or different, represent straight or branched alkylene chains, these may be, for example, methylene, ethylene, 1-methylethylene, propylene, 2-methylpropylene or butylene. In addition, E may represent a chemical bond such that the moiety Z is attached directly to the indoline or azaindoline ring system.

Suitable values for the substituent $R^1$ include benzyl, phenylethyl, imidazolylmethyl and pyridylmethyl, any of which groups may be optionally substituted by one or more substituents selected typically from halogen, $C_{1-6}$ alkoxy, amino, $C_{2-6}$ alkylcarbonylamino, $C_{1-6}$ alkylsulphonylamino and $C_{1-6}$ alkylaminosulphonylmethyl. Particular values of $R^1$ include benzyl, fluorobenzyl, difluorobenzyl, methoxybenzyl, aminobenzyl, acetylamino-benzyl, phenylethyl, fluoro-phenylethyl, difluoro-phenylethyl, acetylamino-phenylethyl and pyridylmethyl.

Suitably, $R^2$ represents hydrogen or methyl, especially hydrogen.

A particular sub-class of compounds according to the invention is represented by the compounds of formula II, and salts and prodrugs thereof:

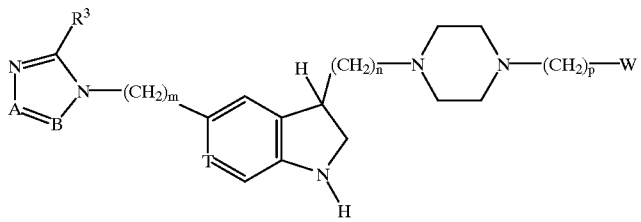

(II)

wherein
m is zero, 1, 2 or 3;
n is 2, 3, 4 or 5, preferably 3 or 4;
p is 1, 2 or 3;
T represents nitrogen or CH;
A represents nitrogen or CH;
B represents nitrogen or C—$R^4$;
$R^3$ and $R^4$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano or trifluoromethyl; and
W represents a group of formula (a), (b) or (c):

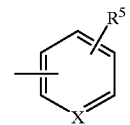 (a)

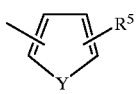 (b)

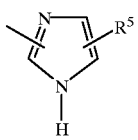 (c)

in which
X represents CH or nitrogen;
Y represents oxygen, sulphur or NH; and
$R^5$ represents hydrogen, halogen, cyano, trifluoromethyl, $C_{1-6}$ alkoxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino or $C_{1-6}$ alkylaminosulphonylmethyl.

Particular values of $R^3$ and $R^4$ include hydrogen, methyl, ethyl, benzyl and amino, especially hydrogen.

Particular values of $R^5$ include hydrogen, fluoro, methoxy, amino and acetylamino.

In one embodiment of the compounds of formula II as defined above, T represents CH.

Specific compounds within the scope of the present invention include:
4-benzyl-1-[3-(2,3-dihydro-5-(1,2,4-triazol-4-yl)-1H-indol-3-yl)propyl]piperazine;
1-[3-(2,3-dihydro-5-(1,2,4-triazol-4-yl)-1H-indol-3-yl) propyl]-4-(pyridin-3-ylmethyl)piperazine;
and salts and prodrugs thereof.

Additional specific compounds within the scope of the present invention also include:
4-benzyl-1-[3-(2,3-dihydro-5-(1,2,4-triazol-1-yl)-1H-pyrrolo[2,3-c]pyridin-3-yl)propyl]piperazine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises N-alkylation of a compound of formula III:

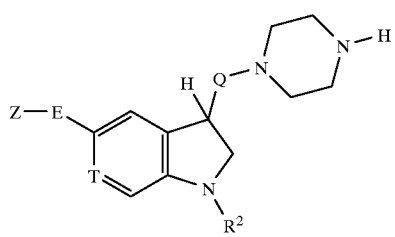
(III)

wherein Z, E, Q, T and $R^2$ are as defined above.

Attachment of the $R^1$ moiety to the compounds of formula III may conveniently be effected by standard alkylation techniques, for example by treatment with an aryl($C_{1-6}$)alkyl or heteroaryl($C_{1-6}$)alkyl halide such as benzyl iodide, benzyl bromide or 3-(chloromethyl)pyridine, typically under basic conditions, e.g. sodium hydride or potassium carbonate in N,N-dimethylformamide, or triethylamine in acetonitrile. Alternatively, the $R^1$ moiety may conveniently be attached by a reductive alkylation procedure, which comprises treating the required compound of formula III as defined above with the appropriate aldehyde, e.g. benzaldehyde, in the presence of a reducing agent such as sodium cyanoborohydride.

The compounds of formula III above may be prepared by reducing a compound of formula IV:

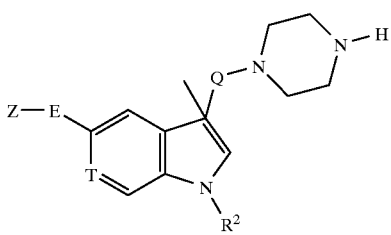
(IV)

wherein Z, E, Q, T and $R^2$ are as defined above.

Reduction of compound IV is conveniently effected by catalytic hydrogenation using hydrogen in the presence of a suitable catalyst, e.g. palladium on carbon, typically at an elevated pressure, e.g. a pressure in the region of 60 psi, and advantageously under acidic conditions, e.g. as a solution in 4M hydrochloric acid.

The compounds of formula IV above wherein T represents CH may be prepared by a process which comprises reacting a compound of formula V:

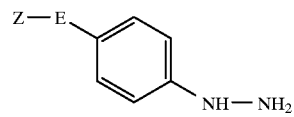
(V)

wherein Z and E are as defined above; with a compound of formula VI, or a carbonyl-protected form thereof:

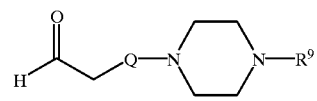
(VI)

wherein Q is as defined above, and $R^P$ represents an amino-protecting group; followed, where required, by N-alkylation by standard methods to introduce the moiety $R^2$; with subsequent removal of the amino-protecting group $R^P$.

The reaction between compounds V and VI, which is an example of the well-known Fischer indole synthesis, is suitably carried out by heating the reagents together under mildly acidic conditions, e.g. 4% sulphuric acid at reflux.

Suitable carbonyl-protected forms of the compounds of formula VI include the dimethyl acetal derivatives.

The protecting group $R^P$, in the compounds of formula VI is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds V and VI may be carried out in a single step, or may proceed via an initial non-cyclising step at a lower temperature to give an intermediate of formula VII:

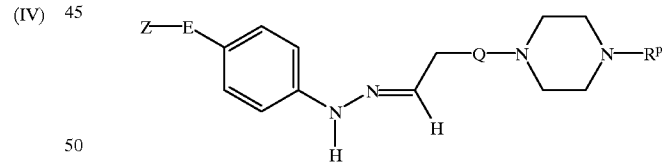
(VII)

wherein Z, E, Q and $R^P$ are as defined above; followed by cyclisation using a suitable reagent, e.g. a polyphosphate ester.

The intermediates of formula VI, or carbonyl-protected forms thereof, may be prepared by reacting a compound of formula VIII, or a carbonyl-protected form thereof, with a compound of formula IX:

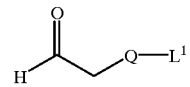
(VIII)

-continued (IX)

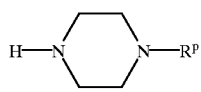

(XI)

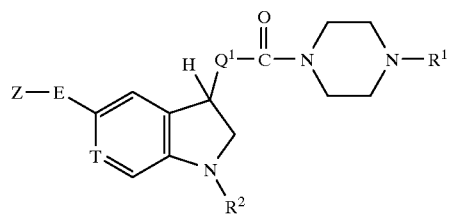

wherein Q and $R^P$ are as defined above, and $L^1$ represents a suitable leaving group.

The leaving group $L^1$ is suitably a halogen atom, e.g. chlorine or bromine.

Where $L^1$ represents a halogen atom, the reaction between compounds VIII and IX is conveniently effected by stirring the reactants under basic conditions in a suitable solvent, for example sodium carbonate in dimethoxyethane, potassium carbonate in N,N-dimethylformamide, or triethylamine in tetrahydrofuran or acetonitrile, optionally in the presence of catalytic sodium iodide.

In an alternative procedure, the compounds of formula IV above may be prepared by reacting a compound of formula IX as defined above with a compound of formula X:

(X)

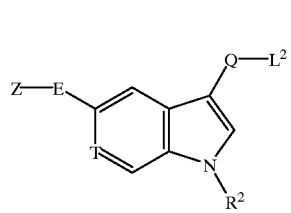

wherein Z, E, Q, T and $R^2$ are as defined above, and $L^2$ represents a suitable leaving group; followed by removal of the amino-protecting group $R^P$.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds IX and X is conveniently carried out in a suitable solvent such as 1,2-dimethoxyethane, typically in the presence of a base such as sodium carbonate.

In a representative embodiment, the compounds of formula X wherein T represents CH, $R^2$ is hydrogen, Q represents a propylene chain and $L^2$ represents a mesyloxy or tosyloxy group may be prepared by reacting 3,4-dihydro-2H-pyran with a compound of formula V as defined above or a salt thereof, under a variant of the Fischer reaction conditions as described above for the reaction between compounds V and VI; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating an acid addition salt of the hydrazine derivative V, typically the hydrochloride salt, in an inert solvent such as dioxan, at the reflux temperature of the solvent.

The compounds according to the invention may also be prepared by a process which comprises reducing a compound of formula XI:

wherein Z, E, T, $R^1$ and $R^2$ are as defined above, and $-Q^1-CH_2-$ corresponds to the moiety Q as defined above.

The reaction is suitably carried out by treating the compound of formula XI with a reducing agent such as lithium aluminium hydride in an appropriate solvent, e.g. diethyl ether or tetrahydrofuran, or mixtures thereof.

The compounds of formula XI above may suitably be prepared by reacting a compound of formula XII with a compound of formula XIII:

(XII)

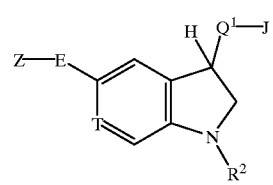

(XIII)

wherein Z, E, T, $R^1$, $R^2$ and $Q^1$ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XII above wherein J is an acid chloride moiety may be prepared by treating the corresponding carboxylic acid derivative with thionyl chloride in toluene. Similarly, the intermediates of formula XII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XIII.

The hydrazine derivatives of formula V above may be prepared by methods analogous to those described in EP-A-0438230 and EP-A-0497512.

Where they are not commercially available, the starting materials of formula VIII, IX, XII and XIII may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^2$ is hydrogen initially obtained may be converted into a compound of formula I wherein $R^2$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D\alpha}$ receptor subtype, inhibit forskolin-stimulated adenylyl cyclase activity, and stimulate [$^{35}$S]-GTPδS binding to membranes from clonal cell lines expressing human cloned receptors.

$5\text{-HT}_{1D\alpha}/5\text{-HT}_{1D\beta}$ Radioligand Binding

Chinese hamster ovary (CHO) clonal cell lines expressing the human $5\text{-HT}_{1D\alpha}$ and $5\text{-HT}_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/ 0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D\alpha}$ receptor subtype obtained for the compounds of the accompanying Examples were 50 nM or less in each case. Furthermore, the compounds of the accompanying Examples were all found to possess a selective affinity for the $5\text{-HT}_{1D\alpha}$ receptor subtype of at least 10-fold relative to the $5\text{-HT}_{1D\beta}$ subtype.

$5\text{-HT}_{1D\alpha}/5\text{-HT}_{1D\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D\alpha}$ and $5\text{-HT}_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 mil preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and EC50 (the molar concentration of compound necessary to inhibit the maximal effect by 50%) values were obtained for each test compound. Of those compounds which were tested in this assay, the $EC_{50}$ values for the $5\text{-HT}_{1D\alpha}$ receptor obtained for the compounds of the accompanying Examples were 500 nM or less in each case. Moreover, the compounds of the accompanying Examples which were tested were all found to possess at least a 10-fold selectivity for the $5\text{-HT}_{1D\alpha}$ receptor subtype relative to the $5\text{-HT}_{1D\beta}$ subtype.

$5\text{-HT}_{1D\alpha}/5\text{-HT}_{1D\beta}$ GTPδS Binding

Studies were performed essentially as described in *Br. J. Pharmacol.*, 1993, 109, 1120. CHO clonal cell lines expressing the human cloned $5\text{-HT}_{1D\alpha}$ and $5\text{-HT}_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40

μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [$^{35}$S]-GTPδS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50% values) were obtained for each test compound. Of those compounds which were tested in this assay, the EC$_{50}$ values for the 5-HT$_{1D\alpha}$ receptor obtained for the compounds of the accompanying Examples were 500 nM or less in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

4-Benzyl-1-(3-(2,3-dihydro-5-(1,2,4-triazol-4-yl)-1H-indol-3-yl)propyl)piperazine 1. Intermediate 1: 5-(4-tert-Butyloxycarbonyl)piperazin-1-ylpentanal dimethyl acetal.

a) 5-Bromopentanal dimethyl acetal

To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated Na$_2$CO$_3$ solution (×1), water (×1) and brine (×2), dried (Na$_2$SO$_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added K$_2$CO$_3$ solution (50 ml) and diethyl ether (500 ml). The aqueous layer was separated and re-extracted with ether (×2). The combined extracts were washed with water and brine, dried (Na$_2$SO$_4$) and evaporated. The crude product was chromatographed on silica gel eluting with diethyl ether/hexane (1:9) to give the title-acetal (27.5 g, 57%). δ (250 MHz, CDCl$_3$) 1.43–1.67 (4H, m, 2 of CH$_2$); 1.83–1.94 (2H, m, CH$_2$); 3.38 (6H, s, CH(OMe)$_2$); 3.42 (2H, t, J=7 Hz, CH$_2$Br), 4.37 (1H, t, J=7 Hz, CH(OMe)$_2$).

b) 5-(4-tert-Butyloxycarbonyl)piperazin-1-yl pentanal dimethyl acetal

A mixture of 5-bromovaleraldehyde dimethyl acetal (27.5 g, 0.13 mol), Na$_2$CO$_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250 MHz, CDCl$_3$) 1.29–1.71 (6H, m, 3 of CH$_2$); 1.46 (9H, s, OC(Me)$_3$); 2.31–2.39 (6H, m, 3 of CH$_2$); 3.32 (6H, s, CH(OMe)$_2$); 3.41–3.45 (4H, m, 2 of CH$_2$); 4.36 (1H, t, J=6 Hz, CH(OMe)$_2$).

2. Intermediate 2: 4'-(1,2,4-Triazol-4-yl)phenylhydrazine a) 4'-Aminoacetanilide A solution of 4-nitroacetanilide (5.0 g, 27.8 mmol) in EtOH/EtOAc (160 ml, 1:1), H$_2$O (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in H$_2$O, basifying with 2N NaOH and extracting into EtOAc. The combined extracts were dried (MgSO$_4$) and evaporated to give the title-aniline (3.75 g, 90%). δ (250 MHz, CDCl$_3$/d$_4$-MeOH) 2.10 (3H, s, Me); 6.68 (2H, d, J=8.8 Hz, Ar-H); 7.27 (2H, d, J=8.8 Hz, Ar-H).

b) 4'-(1,2,4-Triazol-4-yl)acetanilide

A mixture of the preceding aniline (3.52 g, 23.4 mmol), N,N-dimethylformamide azine (3.33 g, 23.4 mmol; *J. Chem. Soc.* (C) 1967, 1664) and p-toluenesulphonic acid monohydrate (0.223 g, 1.17 mmol), in anhydrous toluene (100 ml) was heated at reflux for 17 h. The beige coloured precipitate was filtered off and washed with toluene and CH$_2$Cl$_2$ and dried under vacuum to give the desired triazole (4.29 g, 91%); δ (250 MHz, d$_4$-MeOH/d$_6$-DMSO) 2.14 (3H, s, CH$_3$); 7.60 (2H, d, J=8.8 Hz, Ar-H); 7.78 (2H, d, J=8.8 Hz, Ar-H); 8.96 (2H, s, Ar-H).

c) 4'-(1,2,4-Triazol-4-yl)-phenylaniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with CH$_2$Cl$_2$ (×5). The combined extracts were dried (MgSO$_4$) and evaporated and the residue chromatographed on silica gel, eluting with CH$_2$Cl$_2$/MeOH/NH$_3$ (80:8:1), to give the title-aniline (2.94 g, 76%); δ (250 MHz, CDCl$_3$) 3.80 (2H, s, NH$_2$); 6.71 (2H, d, J=8.8 Hz, Ar-H); 7.08 (2H, d, J=8.8 Hz, Ar-H); 8.36 (2H, s, Ar-H).

d) 4'-(1,2,4-Triazol-4-yl)phenylhydrazine

To a solution of the preceding aniline (1.60 g, 9.99 mmol) in concentrated HCl/H$_2$O (23 ml and 3 ml respectively) was added, at −21° C., a solution of NaNO$_2$ (0.69 g, 9.99 mmol) in H$_2$O (8 ml), at such a rate as to maintain the temperature below −10° C. The mixture was stirred for 0.3 h and then filtered rapidly through a sinter, under vacuum. The filtrate was added to a cooled (−20° C.) solution of SnCl$_2$.2H$_2$O (9.02 g, 40.0 mmol) in concentrated HCl (17 ml). The mixture was stirred at −20° C. for 0.25 h and then at room temperature for 1.25 h. The resulting solid was filtered off, washed with Et$_2$O and dried under vacuum. The crude product was dissolved in H$_2$O, basified with concentrated aqueous NaOH and extracted with EtOAc (×5). The combined extracts were dried (MgSO$_4$) and evaporated to afford the title-product (0.95 g, 54%); δ (250 MHz, CDCl$_3$/d$_4$-MeOH) 3.98 (3H, br s, NH and NH$_2$); 6.97 (2H, d, J=12.0 Hz, Ar-H); 7.25 (2H, d, J=12.0 Hz, Ar-H); 8.48 (2H, s, Ar-H).

3. 1-(3-(5-(1,2,4-Triazol-4-yl)-1 H-indol-3-yl)propyl)-4H-piperazine

A mixture of intermediates 1 (9.03 g, 28.6 mmol) and 2 (5.0 g, 28.6 mmol) in 4% sulphuric acid (300 ml) was heated at reflux for 22 h. The solution was cooled in an ice bath, basified with solid K$_2$CO$_3$ and extracted with butan-1-ol (3 x). The solvent was removed in vacuo and the residue azeotroped with hexane (2 x). The residue was chromatographed on silica eluting with $CH_2Cl_2$:MeOH:$NH_3$ (30:8:1) to give the title indole (3.9 g, 44%) as a beige foam. δ (250 MHz, $CDCl_3$+$d_4$-MeOH) 1.87–1.99 (2H, m), 2.42–2.49 (6H, m), 2.75–2.81 (2H, m), 2.88–2.92 (4H, m), 7.14 (1 H, dd, J=8.6 and 2.1 Hz), 7.18 (1H, s), 7.49 (1H, d, J=8.6 Hz), 7.58 (1H, d, J=2.1 Hz), 8.60 (2H, s).

4. 1-(3-(2,3-Dihydro-5-(1,2,4-triazol-4-yl)-1 H-indol-3-yl)propyl)-4H-piperazine A solution of 1-(3-(5-(1,2,4-triazol-4-yl)-1 H-indol-3-yl)propyl)-4H-piperazine (314 mg, 1.0 mmol) in 4M hydrochloric acid (30 ml) containing palladium on carbon (0.35 g) was hydrogenated at 60 psi for four days. After this time the catalyst was removed by filtration and the filtrate evaporated. The residue was chromatographed on silica, eluting with $CH_2Cl_2$:MeOH:$NH_3$ (40:8:1) to afford the indoline (255 mg, 81%) as a colourless oil. δ(360 MHz, $CDCl_3$) 1.50–1.86 (4H, m), 2.34–2.43 (6H, m), 2.89–2.92 (4H, m), 3.30–3.41 (2H, m), 3.78–3.84 (1H, m), 3.93 (1H, brs), 6.64 (1H, d, J=8.2 Hz), 7.00 (1H, dd, J=8.2 and 2.2 Hz), 7.02 (1H, s), 8.33 (2H, s).

5. 4-Benzyl-1-(3-(2,3-dihydro-5-(1,2,4-triazol-4-yl)-1H-indol-3-yl)propyl)piperazine To a solution of 1-(3-(2,3-dihydro-5-(1,2,4-triazol-4-yl)-1H-indol-3-yl)propyl)-4H-piperazine (115 mg, 0.37 mmol) in anhydrous DMF (5 ml) containing $K_2CO_3$ (101 mg, 0.74 mmol) was added benzyl bromide (44 μl, 0.37 mmol). The mixture was heated at 50° C., under nitrogen for two hours. After this time the solution was cooled to room temperature and the mixture diluted with EtOAc (30 ml) and washed with water (2×20 ml). The organic layer was separated and the aqueous phase extracted with EtOAc (2×10 ml). The combined organic layers were dried ($Na_2SO_4$) and evaporated in vacuo. The residue was chromatographed on silica, eluting with $CH_2Cl_2$:MeOH (90:10), to give the title indoline (80 mg, 54%) as a colourless foam. Found: C, 67.42;H, 7.37; N, 19.38.$C_{24}H_{30}N_6$.1.4($H_2O$) requires: C, 67.39; H, 7.73; N, 19.65. δ (360 MHz, $d_6$-DMSO) 1.40–1.56 (3H, m), 1.73–1.82 (1H, m), 2.22–2.44 (8H, m), 3.11–3.24 (2 H, m), 3.28–3.38 (2H, m), 3.42 (2H, s), 3.58–3.63 (1H, m), 5.75 (1H, br s), 6.52 (1H, d, J=8.3 Hz), 7.12 (1H, dd, J=8.3 and 2.2 Hz), 7.20–7.32 (6H, m), 8.84 (2H, s).

EXAMPLE 2

1-(3-(2,3-Dihydro-5-(1,2,4-triazol-4-yl)-1H-indol-3-yl)propyl)-4-(pyridin-3-ylmethyl)piperazine oxalate To a suspension of 3-(chloromethyl)pyridine hydrochloride (32 mg, 0.19 mmol) in anhydrous DMF (2 ml) was added sodium hydride (8 mg of a 60% dispersion in mineral oil, 0.19 mmol). The mixture was stirred at 0° C., under nitrogen, for 30 min. After this time the mixture was added to a stirred solution of 1-(3-(2,3-dihydro-5-(1,2,4-triazol-4-yl)-1H-indol-3-yl)propyl)-4H-piperazine (55 mg, 0.18 mmol) and $K_2CO_3$ (48 mg, 0.35 mmol) in DMF (4 ml) at 0° C. The mixture was diluted with DMF (2 ml) then sodium iodide (0.09 mmol, 14 mg) was added and the mixture heated at 60° C. for 4 h. After this time the solvents were removed in vacuo and the residue chromatographed on silica, eluting with $CH_2Cl_2$:MeOH:$NH_3$ (90:10:1) to give the indoline free base (47 mg, 66%) as a colourless oil. The free base was dissolved in ether/MeOH (10/1, 2 ml) and treated dropwise with a solution of oxalic acid (11 mg, 0.12 mmol) in ether. The title indoline (28 mg) which was collected by filtration was isolated as a colourless solid. m.p. 140–142° C. Found: C, 53.24; H, 5.83; N, 16.23.$C_{23}H_{29}N_7$.2.1 ($C_2H_2O_4$).$H_2O$ requires C, 53.50; H, 5.81; N, 16.06. δ (360 MHz, $d_6$-DMSO) 1.43–1.82 (4H, m), 2.42–3.33 (12H, m), 3.61–3.65 (3H, m), 6.56 (1H, d, J=8.3 Hz), 7.16 (1H, dd, J=8.3 and 2.2 Hz), 7.27 (1H, d, J=2.2 Hz), 7.39 (1H, dd, J=8.0 and 4.9 Hz), 7.72 (1H, d, J=7.9 Hz), 8.50 (1H, d, J=4.9 Hz), 8.53 (1H, s), 8.86 (2H, s).

EXAMPLE 3

4-Benzyl-1-[3-(5-(1,2,4-triazol- 1-yl)-2,3-dihydro-1H-pyrrolo[2,3c]pyridin-3-yl)propyl]piperazine oxalate 1. Intermediate 1: 5-(1,2,4-Triazol-1-yl)-1H-pyrrolo[2,3-c]pyridine a) 4-Methyl-5-nitro-2-(1,2,4-triazol-1-yl)pyridine To a solution of 1,2,4-triazole (4.0 g, 58 mmol) in dry DMF (20 mL) was added potassium carbonate (12.0 g, 87 mmol) and 2-chloro-4-methyl-5-nitropyridine (10 g, 58 mmol) and the mixture stirred at ambient temperature under nitrogen for 24 hours. Ethyl acetate (500 mL) and water (250 mL) were added to the mixture and the resulting precipitate was collected by filtration to give the title compound (5.08 g, 43%) as a pale brown solid. The filtrate was separated and the organic phase was washed with water (250 mL) and brine (250 mL), dried ($MgSO_4$) and evaporated. The residue was triturated with ethyl acetate and the precipitate collected by filtration to give the title compound as a brown solid (4.11 g, 35%, overall yield 78%). mp 198–200° C. $^1$H NMR (360 MHz, $CDCl_3$) δ 2.72 (3H, s), 7.86 (1H, s), 8.07 (1H, s) 9.03 (1H, s) and 9.15 (1H, s).

b) N,N-Dimethyl-2-(5-nitro-2-(1,2,4-triazol-1-yl)-pyridin-4-yl)ethenamine

To a suspension of 4-methyl-5-nitro-2-(1,2,4-triazol-1-yl)pyridine (4.1 g, 20 mmol) in dry DMF (30 mL) was added dimethylformamide dimethyl acetal (5.9 mL, 44 mmol) and the mixture heated at 90° C. for 20 min. The solvent was evaporated in vacuo using toluene as an azeotrope to give the title compound (5.2 g, 100%) as a dark red solid. mp 225–228° C. $^1$H NMR (360 MHz, $CDCl_3$) δ 3.10 (6H, s) 6.13 (1H, d, J=13.1 Hz), 7.54 (1H, d, J=13.1 Hz), 7.81 (1H, s) 8.04 (1H, s), 8.92 (1H, s) and 9.17 (1H, s).

c) 5-(1,2,4-Triazol-1-yl)-1H-pyrrolo[2,3-c]pyridine N,N-Dimethyl-2-(5-nitro-2-(1,2,4-triazol-1-yl)pyridin-4-yl) ethenamine (8 g, 31 mmol) was hydrogenated over platinum oxide (1.6 g) in ethanol (150 mL) at 30 psi of hydrogen for 1 hour. The catalyst was removed by filtration and the solvent evaporated in vacuo. The residue was chromatographed on silica eluting with ethyl acetate to afford an orange/brown solid. This was triturated with ether and the precipitate collected by filtration to give the title compound (2.89 g, 51%) as a pink solid. mp 203–205° C. $^1$H NMR (360 MHz, $d_6$-DMSO) δ 6.67 (1H, d, J=3.0 Hz), 7.76 (1H, d, J=2.9 Hz), 8.01 (1H, s), 8.23 (1H, s), 8.70 (1H, s), 9.25 (1H, s) and 11.86 (1H, br s).

2. 3-Formyl-5-(1,2,4-triazol-1-yl)-1H-pyrrolo[2,3-c]pyridine

A mixture of Intermediate 1 (3.86 g, 20.9 mmol) and hexamethylenetetramine (4.39 g, 31.3 mmol) was refluxed in 33% aqueous acetic acid (35 mL) for 90 min. Water (40 mL) was added and the mixture cooled in ice for 90 min. The precipitate was collected by filtration to give the title compound (3.31 g, 74%) as a beige solid. mp 220° C. (dec.). $^1$H NMR (250 MHz, $d_6$-DMSO) δ 8.29 (1H, s), 8.46 (1H, s), 8.65 (1H, s), 8.81 (1H, s), 9.33 (1H, s), 10.04 (1H, s) and 12.78 (1H, br s).

3. 1-tert-Butyloxycarbonyl-3-formyl-5-(1,2,4-triazol- 1-yl)pyrrolo[2,3-c]pyridine To a solution of 3-formyl-5-(1,2,4-triazol-1-yl)-1H-pyrrolo[2,3-c]pyridine (3.4 g, 16 mmol) in acetonitrile (75 mL) was added di-tert-butyl dicarbonate (4.18 g, 19 mmol) and dimethylaminopyridine (98 mg, 0.8 mmol) and the mixture was stirred at ambient temperature under nitrogen for 16 hours. The solvent was evaporated in vacuo and the residue triturated with ether. The precipitate was collected by filtration and chromatographed on silica eluting with 20% EtOAc in DCM to give the title compound (3.98 g, 70%) as a colourless solid. mp 190° C. (dec.). $^1$H NMR (360 MHz, d$_6$-DMSO) δ 1.70 (9H, s), 8.33 (1H, s), 8.51 (1H, s), 9.00 (1H, s), 9.20 (1H, s), 9.41 (1H, s) and 10.15 (1H, s).

4. Ethyl 3-[1-tert-butyloxycarbonyl-5-(1,2,4-triazol-1-1-yl)pyrrolo[2,3-c]pyridin-3-yl]prop-2-enoate A solution of 1-tert-butyloxycarbonyl-3-formyl-5-(1,2,4-triazol-1-yl)pyrrolo[2,3-c]pyridine (1.5 g, 4.8 mmol) and (carboethoxymethylene)triphenylphosphorane (2.0 g, 5.8 mmol) in toluene (30 mL) was heated at 80° C. under nitrogen for 90 min. The mixture was allowed to cool and the solvent was evaporated in vacuo. The residue was chromatographed on silica eluting with 20% EtOAc in DCM to give a colourless solid. This was triturated with ether and the solid rechromatographed on silica with 20% EtOAc in DCM to give the title compound (1.77 g, 96%) as a colourless solid. mp 178–181° C. 1H NMR (360 MHz, CDCl$_3$) δ 1.37 (3H, t, J=7.1 Hz), 1.73 (9H, s), 4.31 (2H, q, J=7.1 Hz), 6.59 (1H, d, J=16.2 Hz), 7.81 (1H, d, J=16.2 Hz), 8.03 (1H, s), 8.14 (1H, s), 8.30 (1H, s), 9.21 (1H, s) and 9.26 (1H, br s).

5. Ethyl 3-(5-(1,2,4-triazol-1-yl)-2,3-dihydro-1H-pyrrolo[2,3-c]pyridin-3-yl)propionate Ethyl 3-[1-tert-butyloxycarbonyl-5-(1,2,4-triazol-1-yl)pyrrolo[2,3-c]pyridin-3-yl]prop-2-enoate (0.29 g) was hydrogenated over palladium on carbon (10%, 0.435 g) in ethanol (50 mL) at 50 psi of hydrogen for 75 min. The catalyst was removed by filtration and the solvent evaporated in vacuo to give the title compound. (0.24 g) as a colourless solid. This was used without further purification in the next step.

A solution of the crude ethyl 3-[1-tert-butyloxycarbonyl-5-(1,2,4-triazol-4-yl)-2,3-dihydro-1H-pyrrolo[2,3-c]pyridin-3-yl]propionate (0.24 g, 0.62 mmol) and trifluoroacetic acid (4 mL) in dry DCM (16 mL) was stirred at ambient temperature under nitrogen for 16 hours. The solvent was evaporated in vacuo and the residue azeotroped with toluene. The residue was chromatographed on silica eluting with a gradient of 2 to 5% MeOH in DCM to give the title compound (44 mg, 20%) as a yellow gum. $^1$H NMR (360 MHz, CDCl$_3$) δ 1.27 (3H, t, J=7.1 Hz), 1.90–2.01 (1H, m), 2.17–2.27 (1H, m), 2.40–2.45 (2H, m), 3.34–3.46 (2H, m), 3.82 (1H, t, J=8.6 Hz), 4.15 (2H, q, J=7.1 Hz), 7.66 (1H, s), 7.73 (1H, s), 8.04 (1H, s) and 8.99 (1H, s).

6. 3-(5-(1,2,4-Triazol-1-yl)-2,3-dihydro-1H-pyrrolo[2,3-c]pyridin-3-yl)propanoic acid (4-benzylpiperazinyl)amide To a solution of ethyl 3-(5-(1,2,4-triazol-1-yl)-2,3-dihydro-1H-pyrrolo[2,3-c]pyridin-3-yl)propionate (0.12 g, 0.42 mmol) in methanol (5 mL) was added NaOH (4M, 0.3 mL) and the mixture was heated at 50° C. for 4 hours. After cooling the solution was neutralised (6M, HCl) and the solvents evaporated in uacuo to give 3-(5-(1,2,4-triazol-1-yl)-1H-pyrrolo[2,3-c]pyridin-3-yl)propionic acid (0.65 g) as a yellow solid. This was used without purification in the next step.

To a suspension of 3-(5-(1,2,4-triazol-1-yl)-2,3-dihydro-1H-pyrrolo[2,3-c]pyridin-3-yl)propionic acid (0.108 g) in dry DMF (3 mL) was added 1-benzylpiperazine (0.11 mL, 0.63 mmol), 1-hydroxybenzotriazole (71 mg, 0.63 mmol), 1-ethyl-3-[3-(dimethylamino)propyl]carbodiimide hydrochloride (0.1 g, 0.52 mmol) and triethylamine (73 μL, 0.52 mmol) and this mixture was stirred at ambient temperature under nitrogen for 64 hours. The solvent was evaporated in vacuo and the residue was partitioned between ethyl acetate (25 mL) and water (25 mL). The two phases were separated and the aqueous phase was extracted with ethyl acetate (2×20 mL). The combined organics were dried (Na$_2$SO$_4$) and evaporated in vacuo. The residue was chromatographed on silica eluting with a gradient of 2 to 5% MeOH in DCM, followed by 95:5:1, DCM:MeOH:NH$_3$ to give the title compound (0.126 g, 72%) as a pale yellow foam. $^1$H NMR (360 MHz, CDCl$_3$) δ 1.88–1.96 (1H, m), 2.07–2.15 (1H, m), 2.30–2.40 (6H, m), 3.28–3.60 (8H, m), 3.72–3.83 (2H, m), 7.19–7.27 (5H, m), 7.57 (1H, s), 7.66 (1H, s), 7.95 (1H, s) and 8.91 (1H, s).

7. 4-Benzyl-1-[3-(5-(1,2,4-triazol-1-yl)-2,3-dihydro-1H-pyrrolo[2,3-c]pyridin-3-yl)propyl]piperazine oxalate To a solution of LiAlH$_4$ in ether (1.0M, 0.86 mL, 0.86 mmol) and dry THF (5 mL) was added dropwise a solution of 3-(5-(1,2,4-triazol-1-yl)-2,3-dihydro-1H-pyrrolo[2,3-c]pyridin-3-yl)propionic acid (4-benzylpiperazinyl)amide (0.12 g, 0.29 mmol) in dry THF (5 mL) at ambient temperature. The mixture was stirred at ambient temperature for 15 min. After cooling water (34 μL) was added followed by sodium hydroxide (4M, 34μL), followed by water (102 μL). The solid was removed by filtration and the solvent evaporated in vacuo. The residue was chromatographed on silica eluting with a gradient of 5 to 10% MeOH in DCM followed by 90:10:1, DCM:MeOH:NH$_3$ to give the free base (16 mg, 14%) as a colourless gum. The free base was dissolved in Et$_2$O:MeOH (10:1, 5 mL) and treated dropwise with a solution of oxalic acid (3.6 mg, 0.04 mmol) in ether (2 mL). The precipitate formed was collected by filtration to give the title compound (12 mg) as a cream solid. mp 135° C. (dec.). Found: C, 54.59; H, 5.85; N, 16.19, C$_{23}$H$_{29}$N$_7$•2(CO$_2$H)$_2$•0.6(H$_2$O) requires C, 54.56; H, 5.80; N, 16.50%. $^1$H NMR (360 MHz, d$_6$-DMSO) δ 1.50–1.86 (4H, m), 2.56–3.30 (10,m), 3.32–3.44 (2H, m), 3.56–3.68 (3H, m), 7.30–7.39 (5H, m), 7.57 (1H, s), 7.66 (1H, s), 8.17 (1H, s) and 9.10 (1H, s).

We claim:

1. A compound of formula II, and pharmaceutically acceptable salts thereof:

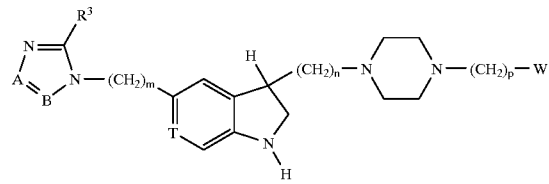

(II)

wherein m is zero or 1;

n is 3 or 4;

p is 1 or 2;

T represents nitrogen or CH;

A represents nitrogen or CH;

B represents nitrogen or C—R⁴;

R³ and R⁴ both represent hydrogen; and

W represents a group of formula (a);

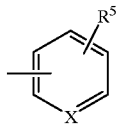

in which

X represents CH or nitrogen; and

R⁵ represents hydrogen, fluoro, methoxy, amino or acetylamino.

2. A compound as claimed in claim 1 wherein T represents CH.

3. A compound selected from:

4-benzyl-1-[3-(2,3-dihydro-5-(1,2,4-triazol-4-yl)-1H-indol-3-yl)propyl]piperazine;

1-[3-(2,3-dihydro-5-(1,2,4-triazol-4-yl)-1H-indol-3-yl)propyl]-4-(pyridin-3-ylmethyl)piperazine;

and pharmaceutically acceptable salts thereof.

4. A compound selected from:

4-benzyl-1-[3-(2,3-dihydro-5-(1,2,4-triazol-1-yl)-1H-pyrrolo[2,3-c]pyridin-3-yl)propyl]piperazine;

and pharmaceutically acceptable salts thereof.

5. A pharmaceutical composition comprising a compound as claimed in claim 1 in association with a pharmaceutically acceptable carrier.

6. A method for the treatment and/or prevention of migraine, cluster headache, chronic paroxysmal hemicrania, headache associated with vascular disorders, tension headache, and pediatric migraine, which method comprises administering to a patient in need of such treatment an effective amount of a compound as claimed in claim 2.

* * * * *